US00PP30148P2

(12) United States Plant Patent
Watanabe

(10) Patent No.: US PP30,148 P2
(45) Date of Patent: Jan. 29, 2019

(54) ***HYDRANGEA* PLANT NAMED 'LITTLE EMA'**

(50) Latin Name: *Hydrangea paniculata*
Varietal Denomination: Little Ema

(71) Applicant: Kenji Watanabe, Kanuma (JP)

(72) Inventor: Kenji Watanabe, Kanuma (JP)

( * ) Notice: Subject to any disclaimer, the term of this patent is extended or adjusted under 35 U.S.C. 154(b) by 0 days.

(21) Appl. No.: 15/732,613

(22) Filed: Dec. 1, 2017

(51) Int. Cl.
*A01H 5/02* (2018.01)

(52) U.S. Cl.
USPC ..... Plt./250

(58) Field of Classification Search
USPC ..... Plt./250
CPC ..... A01H 6/48
See application file for complete search history.

*Primary Examiner* — Keith O. Robinson
(74) *Attorney, Agent, or Firm* — Audrey Charles

(57) ABSTRACT

A new and distinct cultivar of *Hydrangea* plant named 'Little Ema', characterized by its white-colored inflorescences, medium green-colored foliage, and moderately vigorous, compact, upright-mounded growth habit, is disclosed.

1 Drawing Sheet

Latin name of genus and species of plant claimed: *Hydrangea paniculata.*

Variety denomination: 'Little Ema'.

BACKGROUND OF THE INVENTION

The present invention relates to a new and distinct cultivar of *Hydrangea* plant botanically known as *Hydrangea paniculata* and hereinafter referred to by the cultivar name 'Little Ema'.

The new cultivar originated in a controlled breeding program in Kanuma-shi, Japan during July 2007. The objective of the breeding program was the development of *Hydrangea* cultivars that are floriferous with a compact growth habit.

The new *Hydrangea* cultivar was the result of a self-pollination of the proprietary *Hydrangea paniculata* breeding selection coded HNW, not patented, characterized by its white-colored inflorescences, light green-colored foliage, low growth vigor, and compact, upright-mounded growth habit. The new cultivar was discovered and selected as a single flowering plant within the progeny of the above stated self-pollination during July 2010 in a controlled environment in Kanuma-shi, Japan.

Asexual reproduction of the new cultivar by softwood cuttings since July 2010 in Kanuma-shi, Japan and Hillegom, The Netherlands has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Little Ema' as a new and distinct cultivar of *Hydrangea* plant:

1. White-colored inflorescences;
2. Medium green-colored foliage; and
3. Moderately vigorous, compact, upright-mounded growth habit.

Plants of the new cultivar differ from plants of the parent primarily in having more growth vigor and darker green-colored foliage.

Of the many commercially available *Hydrangea* cultivars, the most similar in comparison to the new cultivar is 'Daruma', not patented. However, in comparison, plants of the new cultivar differ from plants of 'Daruma' in at least the following characteristics:

1. Plants of the new cultivar have a more compact growth habit than plants of 'Daruma'; and
2. Plants of the new cultivar have a darker foliage color than plants of 'Daruma'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Little Ema'. The plants were three-years old and were grown in the field for the final two years in Hillegom, The Netherlands. Plants were given one pinch six months after sticking. Plants were transferred to a 27 cm pot for photographic purposes.

DETAILED BOTANICAL DESCRIPTION

Figure 1:
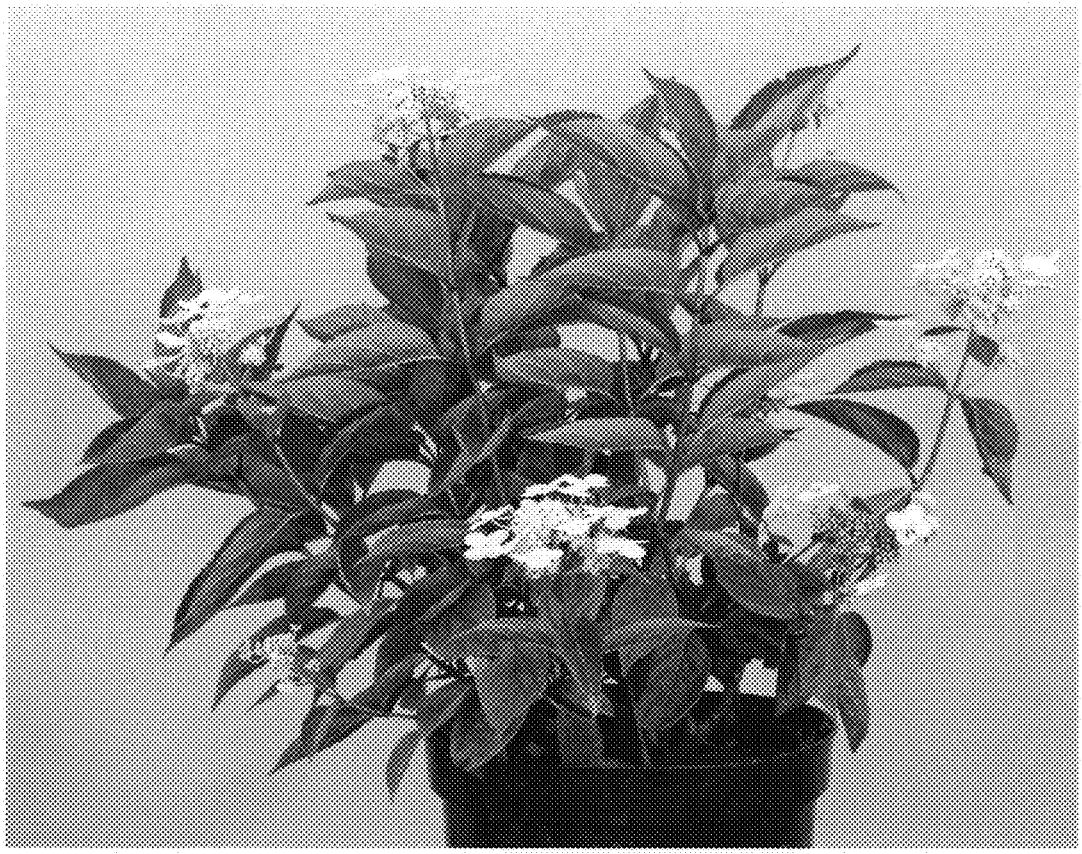
FIG. 1 illustrates a side view of the overall growth and flowering habit of 'Little Ema'.
Figure 2:
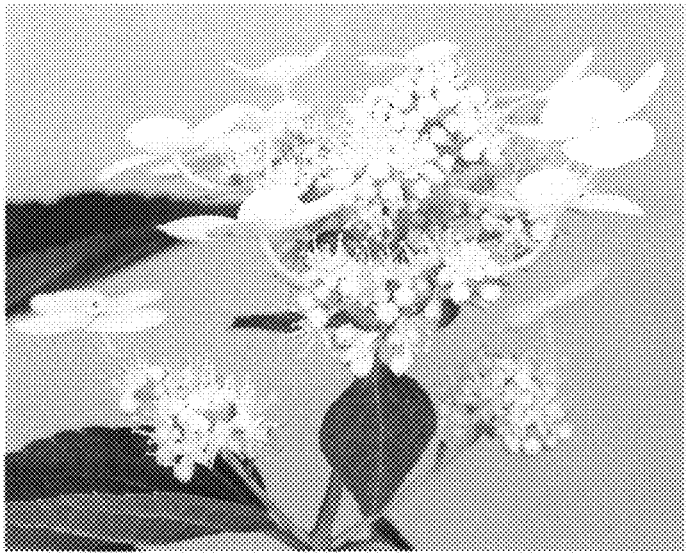
FIG. 2 illustrates a close-up view of an individual inflorescence of 'Little Ema'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2017 under natural light conditions in Boskoop, The Netherlands.

The following descriptions and measurements describe 3-year old plants produced in Hillegom, The Netherlands from softwood cuttings from stock plants. Plants were grown for one year in a poly-covered greenhouse under conditions comparable to those used in commercial practice. Plants were given one pinch six months after sticking. The plants were grown in the field for the final two years in Hillegom, The Netherlands. Measurements and numerical values represent averages of typical plants.

Botanical classification: *Hydrangea paniculata* 'Little Ema'.

Parentage:

*Female and male parent.*—Proprietary *Hydrangea paniculata* breeding selection coded HNW, not patented.

Propagation:

*Type cutting.*—Softwood.

*Time to initiate roots.*—Approximately 25 to 30 days.

*Time to produce a rooted cutting.*—Approximately 35 to 50 days.

*Root description.*—Medium thickness, white in color.

*Rooting habit.*—Freely branching, dense.

Plant description:

*Commercial crop time.*—Approximately 12 to 14 weeks from a rooted cutting to finish in a 18 cm pot.

*Growth habit and general appearance.*—Deciduous shrub, moderately vigorous, compact, upright-mounded.

*Hardiness.*—USDA Zone 5a (−20° F. to −15° F.).

*Heat tolerance.*—Regularly tolerates temperatures as high as 38° C. in the summer.

*Size.*—Height from soil level to top of plant plane: Approximately 48.5 cm. Width: Approximately 63.1 cm.

*Branching habit.*—Moderately freely branching. Pinching enhances branching. Quantity of lateral branches per plant: Approximately 17.

*Branch.*—Shape: Rounded. Strength: Very strong. Length to base of inflorescence: Approximately 22.9 cm. Diameter: Approximately 4.0 mm. Length of central internode: Approximately 5.1 cm. Texture of young stem: Glabrous. Texture of mature stem: Glabrous, becomes woody with age. Color of young stem: 146D and 147D with an overlay of 182D. Color of mature stem: 146D and 147D with an overlay of 182D and 185C, when woody N200B.

*Lenticels.*—Quantity per internode: Approximately 15. Shape: Narrow elliptic. Size: Approximately 1.0 mm. Color: 184D.

Foliage description:

*General description.*—Quantity of leaves per lateral branch: Approximately 10. Fragrance: None detected. Form: Simple. Arrangement: Opposite.

*Leaves.*—Shape: Ovate. Margin: Serrated. Apex: Acuminate. Base: Rounded. Venation pattern: Pinnate. Length of mature leaf: Approximately 11.4 cm. Width of mature leaf: Approximately 6.0 cm. Texture of upper and lower surfaces: Slightly rugose, sparsely pubescent on venation of lower surface only. Color of upper surface of young foliage: Closest to 144A with 137C, venation of 146D. Color of lower surface of young foliage: 146B with venation of 144B. Color of upper surface of mature foliage: Closest to 137B, venation of 148C. Color of lower surface of mature foliage: Closest to 138B with venation of slightly darker than 147D.

*Petiole.*—Length: Approximately 1.9 cm. Diameter: Approximately 3.0 mm. Texture: Sparsely pubescent. Color: Upper surface 183B and lower surface 182B to lighter than 182D.

Flowering description:

*Flowering habit.*—Early July through August.

*Lastingness of individual inflorescence on the plant.*—Approximately 1.5 months.

Inflorescence description:

*General description.*—Type: Single sterile and fertile flowers arranged on terminal conical panicles, sterile florets face mostly upward. Sterile florets occasionally have visible reproductive parts, but lack an ovary. Quantity of panicles per plant: Approximately 8. Fragrance: Faint, sweet. Aspect: Facing upward and slightly outward. Height: Approximately 9.1 cm. Width: Approximately 11.2 cm. Quantity of fertile florets per inflorescence: Approximately 400. Quantity of sterile florets per inflorescence: Approximately 14.

*Peduncle.*—Strength: Strong. Shape: Round, somewhat flattened in cross-section. Length: Approximately 5.4 cm. Diameter: Approximately 3.0 mm. Texture: Moderately pubescent. Color: 182D transitioning to 145B at distal end.

Floret description:

*General description.*—Type: Single, sterile and fertile.

*Sterile florets, bud just before opening.*—Shape: Ovoid. Length: Approximately 5.0 mm. Diameter: Approximately 4.0 mm. Color: 145B.

*Sterile florets.*—Shape: Rotate, cruciform. Depth: Approximately 5.0 mm. Diameter: Approximately 3.4 cm. Corolla: 4 petals. Shape: Rotate, cruciform. Diameter: Approximately 5.5 mm. Calyx: 4 sepals. Shape: Rotate, cruciform. Diameter: Approximately 3.4 cm.

*Petals, sterile florets.*—Shape: Ovate. Margin: Entire. Apex: Acute. Base: Cuneate. Length: Approximately 3.5 mm. Width: Approximately 2.0 mm. Texture of upper and lower surfaces: Glabrous. Color of upper and lower surfaces: NN155C.

*Sepals, sterile florets.*—Shape: Obovate to nearly orbicular. Margin: Entire. Apex: Rounded. Base: Rounded. Length: Approximately 1.7 cm. Width: Approximately 1.5 cm. Texture of upper and lower surfaces: Glabrous. Color of upper surface when first open: Closest to but more yellow green than 155A. Color of lower surface when first open: 155A. Color of upper surface when fully open: Closest to NN155A with a faint tint of 157D; fall color 145D with an overlay of 185D. Color of lower surface when fully open: Closest to NN155A with a faint tint of 157D; fall color 145D with a heavy overlay of 185D.

*Pedicel, sterile florets.*—Strength: Moderately strong. Aspect: Approximately 60° from peduncle axis. Length: Approximately 1.8 cm. Diameter: Approximately 1.5 mm. Texture: Moderately pubescent with appressed hairs. Color: NN155B.

*Fertile florets, bud just before opening.*—Shape: Obovoid. Length: Approximately 3.0 mm. Diameter: Approximately 3.0 mm. Color: 157B.

*Fertile florets.*—Depth: Approximately 5.0 mm. Diameter: Approximately 9.0 mm. Corolla: 5 petals. Shape: Rotate. Diameter: Approximately 8.0 mm. Calyx: 5 sepals. Shape: Cupped, lower 75% fused. Diameter: Approximately 4.0 mm.

*Petals, fertile florets.*—Shape: Ovate. Margin: Entire. Apex: Acute. Base: Cuneate. Length: Approximately 3.5 mm. Width: Approximately 2.0 mm. Texture of upper and lower surfaces: Glabrous. Color: NN155C; fall color 145A with upper half tinted with 185B.

*Sepals, fertile florets.*—Shape of free portion: Triangular. Margin of free portion: Entire. Apex: Acute. Base: Fused. Length: Approximately 2.25 mm. Width at base of free portion: Approximately 0.2 mm. Texture of upper and lower surfaces: Glabrous. Color of upper and lower surface: 157B to 157C.

*Pedicel, fertile florets.*—Strength: Strong. Aspect: Range from erect to approximately 90° from peduncle axis. Length: Approximately 2.0 mm. Diameter: Approximately 1.0 mm. Texture: Sparsely pubescent with appressed hairs. Color: 157D.

*Reproductive organs.*—Observed in fertile florets and occasionally in the center of sterile florets, sterile florets lack an ovary. Androecium: Stamen quantity: 10 per floret. Stamen length: Approximately 5.0 mm. Filament color: 155C. Anther shape: Kidney-shaped, basally attached. Anther length: Approximately 0.5 mm. Anther color: 194B to 194C. Pollen amount: Sparse. Pollen color: 155A. Gynoecium: Pistil quantity: 1 per floret. Pistil length: Approximately 1.0 mm. Stigma shape: Round. Stigma color: NN155A. Style length: Approximately 0.7 mm, three-lobed. Style color: 160B to 160C. Ovary length: Approximately 0.5 mm. Ovary texture: Glabrous. Ovary color: 157B.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'Little Ema', substantially as herein illustrated and described.

* * * * *